(12) United States Patent
Hildebrandt

(10) Patent No.: US 6,193,752 B1
(45) Date of Patent: Feb. 27, 2001

(54) UROLOGICAL IMPLANT, IN PARTICULAR VASCULAR WALL SUPPORT FOR THE URINARY TRACT

(76) Inventor: Peter Hildebrandt, Henfenfelder Strasse 20, D-90482 Nürnberg (DE)

( * ) Notice: Subject to any disclaimer, the term of this patent is extended or adjusted under 35 U.S.C. 154(b) by 0 days.

(21) Appl. No.: 09/106,175

(22) Filed: Jun. 29, 1998

(30) Foreign Application Priority Data

Jul. 9, 1997 (DE) ............................................ 197 29 279

(51) Int. Cl.⁷ ................................. A61F 2/04; A61L 29/00
(52) U.S. Cl. ........................ 623/11.11; 623/1.46; 604/266
(58) Field of Search ................................. 623/12, 11, 1, 623/2, 11.11, 1.46; 604/266

(56) References Cited

U.S. PATENT DOCUMENTS

| 5,328,954 | 7/1994 | Sarangapani . |
|---|---|---|
| 5,718,726 | 2/1998 | Amon et al. . |

FOREIGN PATENT DOCUMENTS

| 33 29 733 | 3/1985 | (DE) . |
|---|---|---|
| 35 29 758 | 2/1986 | (DE) . |
| 43 36 209 | 3/1995 | (DE) . |
| 44 44 445 | 6/1996 | (DE) . |
| 195 05 070 | 8/1996 | (DE) . |
| 195 33 682 | 3/1997 | (DE) . |
| 0 528 039 | 2/1993 | (EP) . |
| 0 544 259 | 6/1993 | (EP) . |
| 0 554 898 | 8/1993 | (EP) . |
| 0 578 998 | 1/1994 | (EP) . |
| 0 634 152 | 1/1995 | (EP) . |
| 0 656 215 | 6/1995 | (EP) . |
| 0 732 109 | 9/1996 | (EP) . |
| 0 747 069 | 12/1996 | (EP) . |
| WO 94/10938 | 5/1994 | (WO) . |
| WO 96/24392 | 8/1996 | (WO) . |

*Primary Examiner*—David J. Isabella
*Assistant Examiner*—Choon P. Koh
(74) *Attorney, Agent, or Firm*—Browdy and Neimark

(57) ABSTRACT

A urological implant, in particular a vascular wall support for the urinary tract, is provided with
 a substantially tubular, inherently stable carrier,
 a spacer film bonded to the carrier surface, and
 an inhibitor film of a glycosamino glycan bonded to the spacer film.

15 Claims, 2 Drawing Sheets

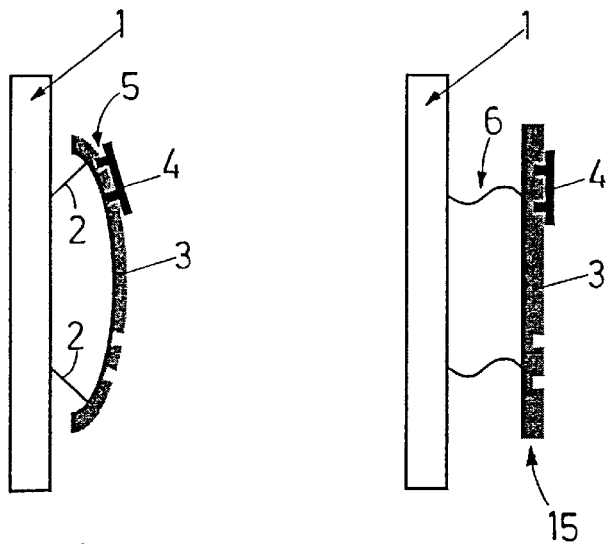
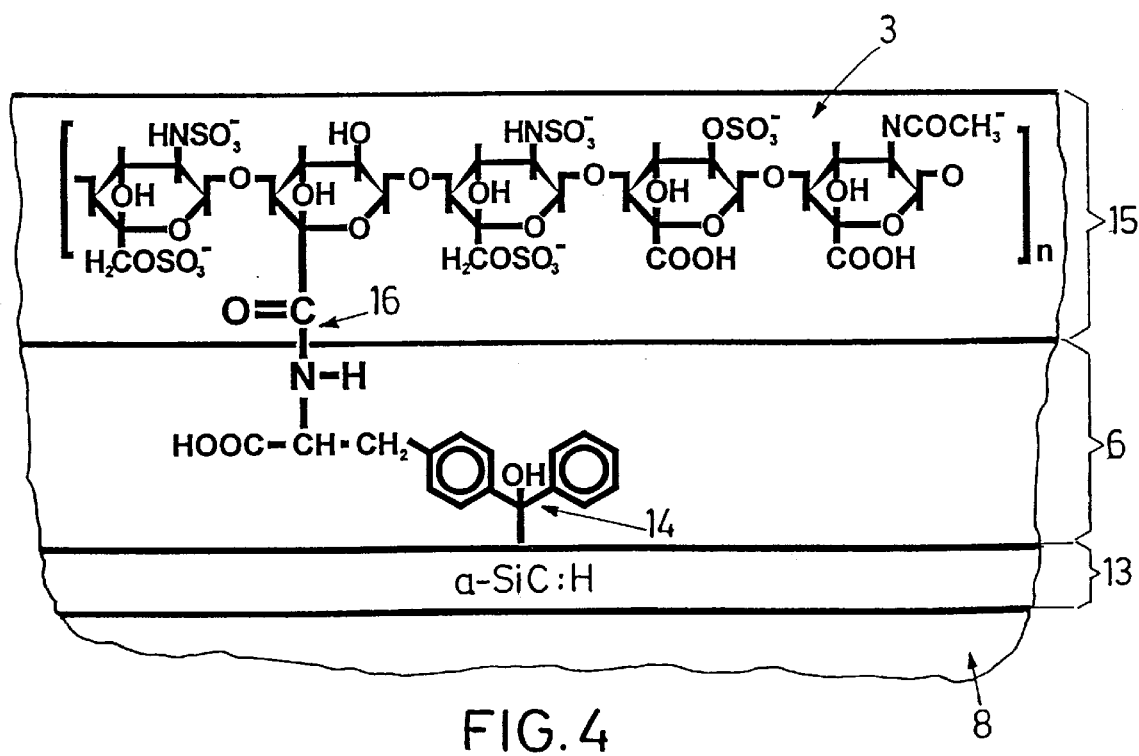
FIG. 1
FIG. 2
FIG. 4

UROLOGICAL IMPLANT, IN PARTICULAR VASCULAR WALL SUPPORT FOR THE URINARY TRACT

BACKGROUND OF THE INVENTION

1. Field of the Invention

The invention relates to a urological implant, in particular a vascular wall support for the urinary tract, such as a urethral, prostate or ureter stent, comprising a substantially tubular, inherently stable carrier. Vascular wall supports of the generic type, which are usually designated as "stents" in technical terminology, are as a rule used for dilating and keeping open pathologically closed or stenotic body vessels. Further examples of application for the urological implants specified are urinary catheters, artificial ureters, artificial urinary diversion systems correspondingly completed by a bladder and so forth.

2. Background Art

To simplify matters, the stents mentioned above will be dealt with below by way of example in the discussion of the prior art and the invention:

Urethral, prostate and ureter stents are indispensable implants for patients with disorders of the urinary tract, if these patients are not in the shape and condition for corresponding surgery. A great variety of stent designs and materials are available today. As a rule, design and material depend on the place where the stent is used and on the implantation technique used. For instance, tubular carriers made from an expansible lattice material are customary. The stent is inserted in its contracted condition via a catheter into the corresponding vessel, where it is expanded for instance by the action of a bubble, its lattice structure extending and the vessel thus being dilated. The stent remains at the place of implantation, serving to support the vascular wall against renewed stenosis.

A serious problem resides in that with all the materials used and tested so far for urinary tract stents, crystallization processes and bacterial colonization will occur on the surface of the stent after several weeks of contact with urine. This leads to serious malfunction of the implants, which strongly jeopardizes the medical success of stent implantation. Numerous studies have dealt with various materials of medicinal technology such as titanium, stainless steel and polymers. However, really durable resistance to crystallize has not been found in any material.

An example of corresponding prior art measures can be seen from U.S. Pat. No. 5 328 954. This document discloses an encrustation and bacterial resistant coating for use on medical devices. The coating includes a reaction product formed by covalent linkage of a hydrophilic polyurethane pre-polymer and aminopolycarboxylic acid. A urease inhibitor and/or antibacterial agent may also be added to the coating.

The aim of this coating—namely to render surfaces resistant to encrustations—is pursued, using antibacterial substances which are bonded on the surface, there preventing a pH increase as produced by bacterial colonization. In this case, encrustations are to be blocked by precipitation of the urine components no longer taking place due to an increased pH.

The substances specified for immobilization are among others ethylene-diamine-tetra-acetate complexes, antibiotics and silver ions, which are ionically or covalently bonded to polyurethanes. As has however been found, the blocking of encrustations achievable by this prior art is still in need of improvement. It is an object of the invention to solve these problems.

SUMMARY OF THE INVENTION

The invention is based on, and proceeds from, natural biomedical processes for stopping crystalline growth in the urinary tract:

Most ionic components of the human urine are present in oversaturated concentrations. Nevertheless, precipitation or formation of greater crystallites does not occur in sound urine. This is prevented by the presence of low- or high-molecular inhibitors. Sodium, potassium, magnesium and citrate ions among others belong to the low-molecular inhibitors, the effectiveness of which is to be rated rather low. The decisive part as inhibitors is played by the macromolecules contained in urine, which can be divided into two groups. They are glycosamino glycans (GAG) and proteins. Heparin, heparene sulfate and various chondroitin sulfates belong to the first group, nephrocalcin, osteopontin and Tamm-Horsfall protein belong to the second. These mentioned macromolecules work through adsorption on molecules and crystal surfaces, thus preventing the growth of greater crystal structures. The action of an inhibitor is mostly restricted to one or few sorts of particles. For instance, nephrocalcin bonds to potassium ions and heparin to oxalate ions and crystallites as substances to be inhibited.

If the inhibitor and the to-be-inhibited substances are present, dissolved in the urine, then there is active effectiveness. If however the urine components under regard adsorb on surfaces, the inhibitors cannot become effective. Owing to the geometric structure of the macromolecules, the linkage between the inhibitor and the substance to be inhibited becomes impossible. The to-be-inhibited substances which adsorb on the surface can virtually serve as crystal germs or seeds from which proceeds a crystallization process. The inhibitors cannot bond to the adsorbed substances either, as a result of which the crystallization process proceeds continuously.

The prevention of chemical linkage as a result of the spatial arrangement of molecules is designated as steric hindrance. Since this steric hindrance occurs on all surfaces, crystalline growth is largely independent of material and surface properties. Appropriate linkage of inhibitors to the substrate however produces a layer on which urine components are bonded as in the urine to be designated as an electrolytic solution. No further components can deposit on urine components thus bonded so that crystalline growth is blocked.

Before the background of these biomedical fundamentals and with a view to solving the problems mentioned at the outset, the invention proposes a urological implant, in particular a vascular wall support for the urinary tract, in which, a spacer molecule film and an inhibitor film bonded thereto of a glycosamino glycan is bonded on the surface of the preferably substantially tubular, inherently stable carrier.

As stated within the scope of the invention, any direct linkage of inhibitors on the carrier surface is not sufficient. Direct linkage will lead to deformations of the macromolecular inhibitors which will prevent bonding between the inhibitor and the substances to be inhibited, i.e. the crystallizing urine components. Inserting the claimed spacer between the carrier surface and the inhibitor film increases the distance between the carrier surface and inhibitor, thus preventing the deformation, explained above, of the molecules and the steric hindrance.

In accordance with preferred embodiments, the carrier may consist of a polymer such as silicone, polyurethane or the like on the one hand, or of tantalum, a titanium alloy, medical steel or pyrolytic carbon on the other hand, in each case with an amorphous silicon carbide coating as an active substrate surface. A configuration of a metal structure with a polymer coating is feasible too. Also the selection of the chemical components of the spacer film is made in dependence on the material properties of the carrier and its substrate surface. In the case of a silicone substrate, the spacer film can be formed on the basis of a propyl-siloxyl compound, in particular a partially substituted 3-(adipinic-acid-amido-)propyl-siloxyl compound. When carriers are used having an amorphous silicon carbide coating as a activated substrate surface, a spacer film on the basis of a photoactive benzophenone compound, in particular a Fmoc-p-Bz-Phe-OH solution in N-N'-dimethylformamide, has proved suitable.

Preferably an immobilized heparin layer is used as an inhibitor film on the spacer film. The heparin layer is deposited and immobilized on the substrate surface for instance by means of a covalent peptide bond. This type of bond is found in particular when the spacer film is realized, as mentioned above, on the basis of a photoactive benzophenone compound.

Summing up, it can be said that experimental studies based on vascular wall supports, which are equipped in accordance with the invention and in which use is made of a silicon-carbide-spacer-heparin complex on a tantalum carrier, show a strong inhibition effect and thus suppression of crystalline growth. No noticeable crystalline deposits were discovered in in-vitro tests by artificial-urine-dipping of corresponding samples for a period of 12 days. The in-vivo behavior of the urinary tract stent according to the invention can be inferred from the result of these in-vitro tests. Due to the fact that the crystallization potential is higher in-vitro, periods of few weeks correspond to periods of several months in in-vivo tests.

The experimental studies have also yielded the fact that the crystallization-suppressing effect of the coating is independent of urine pH, and sufficient long-term stability of the heparin bond to the spacer film.

Further features, details and advantages of the subject matter of the invention will become apparent from the ensuing description of exemplary embodiments of the invention, taken in conjunction with the attached drawings.

BRIEF DESCRIPTION OF THE DRAWINGS

FIGS. 1 and 2 are model drawings of the linkage between the inhibitor and the support without and with a spacer film, FIG. 4 is a diagrammatic illustration of the coating of the stent on the basis of a silicon-carbide-spacer-heparin complex.

DESCRIPTION OF THE PREFERRED EMBODIMENTS

Figure 3:
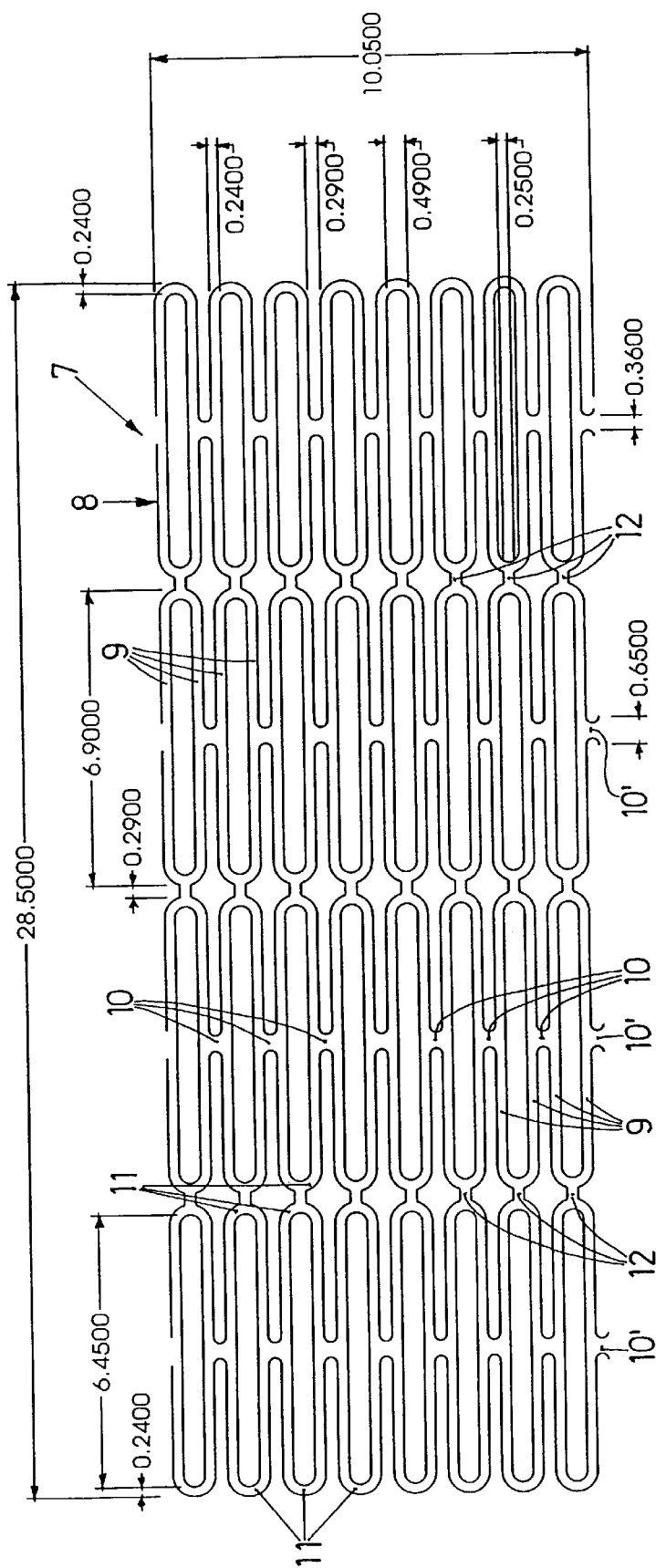
FIG. 3 is a view of a stent structure in an illustration projected on a plane.

FIG. 1 illustrates a substrate 1 to which an inhibitor molecule 3, for instance in the form of heparin, is attached by a direct bond 2. As outlined by way of model, the direct bond 2 leads to deformation of the inhibitor molecule 3, which again results in the fact that the urine component 4, for instance in the form of an oxalate ion, can deposit on the corresponding bonding spots of the heparin. However, this takes place in a virtually incomplete way so that the urine component 4 itself offers bonding spots 5 to which further urine components 4 may attach. This would lead to crystalline growth.

As is to be seen by way of model in FIG. 2, a bond of the inhibitor molecule 3 to the substrate 1 is obtained by the insertion of a spacer film 6 without deformation of the inhibitor molecule 3 taking place. In this regard, the urine component 4 can completely bond to the inhibitor molecule 3 without the urine component 4 being able to offer bonding spots 5. No deposit of further urine components can take place so that the substrate surface is inactivated and resistant to encrustations by a coating of this type.

FIG. 3 shows the typical design of a ureter stent 7 having a carrier 8 of a lattice structure that consists of lengthwise ribs 9 and crosswise ribs 10. The lengthwise ribs 9 are connected by way of semicircular end pieces 11 to form frame units in the form of oblong holes which are again attached to each other by short connecting ribs 12 and the crosswise ribs 10. The illustration selected in FIG. 3 shows a lattice structure cut open, as it were, in the vicinity of the crosswise ribs 10' and spread out into the projection plane of FIG. 3. For clarification of the dimensioning of the vascular wall support according to the invention, corresponding dimensions of the stent and its ribs in millimeters are shown in FIG. 3. Furthermore, attention is drawn to the fact that the lattice structure seen in FIG. 3 corresponds to the non-dilated or non-expanded condition. Upon dilation of the stent, the frames in the form of oblong holes expand rhomboidally, simultaneously becoming shorter.

FIG. 4 illustrates the composition of the silicon-carbide-spacer-heparin complex on the tantalum carrier 8. The latter is provided with a substrate coating 13 of activated silicon carbide (aSiC:H). Attached to this substrate coating 13 is the spacer film 6 which, in a manner still to be explained, is built up on the basis of a photoactive benzophenone bond and is bonded covalently via a C—C or Si—C bond 14 on the surface of the substrate coating 13.

The inhibitor film 15 consists of heparin molecules which are immobilized on the spacer film 6 by way of a peptide bond 16 of its carboxyl groups (O=C—O—H). The inhibitor film 15 is represented by a full-surface heparin layer which is able to bond oxalate ions stably, thus producing an inert cover for the stent surface. Further crystallization processes are thus suppressed.

In the form of a list of individual steps, the following reflects a coating method for the immobilization of heparin on an activated silicon carbide coating. This coating method is fundamentally known from the prior art and specified in detail in the description of the exemplary embodiment of U.S. Pat. No. 5,718,726. There is no need for any renewed summarizing explanation.

| Coating method for the immobilization of heparin on a-SiC | |
|---|---|
| Preparation of sample | |
| Etching with 40% HF | 2 min |
| Rinsing with distilled water | |
| Spacer bonding | |
| Incubation of sample in 2 ml of spacer solution 10 mg Fmoc-p-Bz-Phe-OH in 2 ml dimethyl-formamide (DMF) | |
| Exposure on all sides to ultraviolet light (365 mm) | 1 min |
| Rinsing with distilled water | |
| Splitting off the Fmoc protective group | |
| Incubation of sample in 25% piperidine solution in DMF | 15 min by shaking |
| Incubation of sample in 25% piperidine solution | 15 min by shaking |

-continued

Coating method for the immobilization of heparin on a-SiC

| | |
|---|---|
| Rinsing with distilled water | |
| Heparin bonding | |
| Incubation of sample coated with spacer in 2 ml reaction solution 100 mg heparin, 10 mg carbodiimide, 2 ml distilled water | 4 h |
| Rinsing with distilled water | |

As another exemplary embodiment for the deposit of an active heparin coating on a vascular wall support for the urinary tract, the following shortly illustrates the coating method for the immobilization of heparin on silicone:

| | |
|---|---|
| Production of partially substituted 3-aminopropylsiloxyl-silicone surfaces | |
| Stirring sample in 50 ml ethanol/water | 30 min |
| Stirring at 40° C. in 1 ml 3-aminopropyltiethoxysilane + 49 ml ethanol/water | 16 h |
| Stirring in 50 ml water | 30 min |
| in ethanol/water | 2 h |
| and again in water | 30 min |
| Production of partially substituted 3-(adipinic-acid-amido)-propylsiloxyl silicone surfaces | |
| Stirring at 4° C. in 50 ml water + 365 mg adipinic acid + 50 mg DME-CDI (CME-CDI:N-cyclohexyl-N'-(2-morpholinoethyl)-Carbodiimide-methyl-p-toluosulfate) | 16 h |
| Stirring in water, drying in the air | 30 min |
| Heparin bonding | |
| Stirring at 4° C. in 50 ml buffer pH 5.0 + 50 mg CME-CDI | 30 min |
| Dipping in ice water | 30 sec |
| Stirring at 4° C. in 50 ml buffer pH 5.0 + 100 mg heparin | 16 h |
| Washing in water, drying in the air | |

As for both coating methods shown above in the form of a table, attention is drawn to the fact that they relate to samples for a stent carrier material in the form of a tantalum sample having a coating of amorphous silicon carbide or a sample of silicone material. Of course, the method courses are to be translated directly into the corresponding treatment of stent carriers.

What is claimed is:

1. A urological implant, in particular a vascular wall support for a urinary tract, comprising
a substantially tubular, inherently stable carrier (8) adapted for insertion into a urinary tract to provide a wall support for the urinary tract,
a spacer film (6) bonded to the carrier surface, and
means for inhibiting crystallization of urine components on said carrier and said spacer film, said means comprising an inhibitor film (15) of a glycosamino glycan bonded to the spacer film (6), wherein by the spacer film (16) the glycosamino glycan is bonded in an undeformed condition.

2. An implant according to claim 1, wherein the carrier (8) consists of a polymer.

3. An implant according to claim 1, wherein the carrier consists of metal with a coating of a polymer.

4. An implant according to claim 1, wherein the carrier (8) consists of a material of tantalum, a titanium alloy, medical steel or pyrolytic carbon, having an amorphous silicon-carbide coating (13) as an activated substrate surface.

5. An implant according to claim 2, wherein the spacer film is formed on the basis of a propyl-siloxyl compound.

6. An implant according to claim 5, wherein the spacer film is formed from a partially substituted 3-(adipinic-acid-amido)-propyl-siloxyl compound.

7. An implant according to claim 4, wherein the spacer film (6) is formed on the basis of a photoactive benzophenone compound.

8. An implant according to claim 7, comprising Fmoc-p-Bz-Phe-OH solution in as a said photoactive benzophenone compound.

9. An implant according to claim 1, wherein the inhibitor film (15) is formed from a heparin layer (15) immobilized on the spacer film (6).

10. An implant according to claim 7, wherein a heparin layer is deposited and immobilized as an inhibitor film (15) on the substrate surface by means of a covalent peptide bond.

11. The urological implant of claim 2 wherein said polymer is silicone, polyurethane or polyvinyl chloride.

12. The urological implant according to claim 3 wherein said coating of a polymer comprises silicone, polyurethane or polyvinyl chloride.

13. The urological implant of claim 8 wherein said Fmoc-p-Bz-Phe-OH is applied as a solution in N,N'-dimethyl-formamide.

14. The urological implant of claim 1 wherein said carrier has a lattice structure.

15. The urological implant of claim 14 wherein s aid lattice structure comprises lengthwise ribs (9) and crosswise ribs (10) connected by semi-circular end pieces (11) defining therebetween oblong holes.

* * * * *